United States Patent
Van Bommel

(10) Patent No.: US 12,066,651 B2
(45) Date of Patent: Aug. 20, 2024

(54) LIGHTGUIDE BASED LUMINAIRE FOR DISINFECTION AND ILLUMINATION

(71) Applicant: SIGNIFY HOLDING B.V., Eindhoven (NL)

(72) Inventor: Ties Van Bommel, Horst (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 18/271,687

(22) PCT Filed: Jan. 4, 2022

(86) PCT No.: PCT/EP2022/050066
§ 371 (c)(1),
(2) Date: Jul. 11, 2023

(87) PCT Pub. No.: WO2022/148743
PCT Pub. Date: Jul. 14, 2022

(65) Prior Publication Data
US 2024/0077666 A1    Mar. 7, 2024

(30) Foreign Application Priority Data

Jan. 11, 2021  (EP) ..................................... 21150834

(51) Int. Cl.
*A61L 2/10* (2006.01)
*A61L 2/26* (2006.01)
*F21V 8/00* (2006.01)

(52) U.S. Cl.
CPC .............. *G02B 6/0068* (2013.01); *A61L 2/10* (2013.01); *A61L 2/26* (2013.01); *A61L 2209/12* (2013.01)

(58) Field of Classification Search
CPC ..... G02B 6/0068; A61L 2209/12; A61L 2/10; A61L 2/26
See application file for complete search history.

(56) References Cited

U.S. PATENT DOCUMENTS

2016/0139328 A1\* 5/2016 Hikmet ................... F21S 41/16
                                                              362/84
2018/0154029 A1   6/2018 Shr et al.
(Continued)

FOREIGN PATENT DOCUMENTS

CN      208311977 U    1/2019
CN      209726009 U    12/2019
(Continued)

OTHER PUBLICATIONS

Innovation Q+ NPL Search (Year: 2024).\*

*Primary Examiner* — Anabel Ton

(57) ABSTRACT

The invention provides a light generating system (1000) configured to provide system light (1001), wherein the light generating system (1000) comprises (i) a first light generating device (110), (ii) a second light generating device (120), and (iii) a waveguide (400), wherein: —the waveguide (400) has a first face (401), a second face (402), and a side face (403) bridging the first face (401) and the second face (402); —the first light generating device (110) is configured to generate first device light (111), wherein in an operational mode the first device light (111) has a color point in the visible; the first light generating device (110) is configured to irradiate the side face (403), wherein in an operational mode at least part of the first device light (111) escapes from the waveguide (400) via the first face (401); and—the second light generating device (120) is configured to generate second device light (121), wherein in an operational mode the second device light (121) has a centroid wavelength of at maximum 420 nm, and has a spectral power distribution differing from a spectral power distribution of the first device light (111); the second light generating device (120) is configured upstream of the second face (402); wherein in an operational mode at least part of the (Continued)

second device light (121) is transmitted through the waveguide (400) and escapes from the waveguide (400) via the first face (401).

13 Claims, 4 Drawing Sheets

(56) References Cited

U.S. PATENT DOCUMENTS

| | | | |
|---|---|---|---|
| 2018/0180226 A1 | 6/2018 | Van Bommel et al. | |
| 2018/0193504 A1 | 7/2018 | Kreiner et al. | |

FOREIGN PATENT DOCUMENTS

| | | | |
|---|---|---|---|
| CN | 111450281 | A | 7/2020 |
| DE | 102015207999 | A1 | 11/2016 |
| GB | 2583881 | A | 11/2020 |
| JP | 2014086353 | A | 5/2014 |
| KR | 20120041869 | A | 5/2012 |
| WO | 2003027569 | A1 | 4/2003 |
| WO | 2012059866 | A1 | 5/2012 |
| WO | 2015189615 | A1 | 12/2015 |
| WO | 2018041470 | A1 | 3/2018 |

\* cited by examiner

LIGHTGUIDE BASED LUMINAIRE FOR DISINFECTION AND ILLUMINATION

CROSS-REFERENCE TO PRIOR APPLICATIONS

This application is the U.S. National Phase application under 35 U.S.C. § 371 of International Application No. PCT/EP2022/050066, filed on Jan. 4, 2022, which claims the benefit of European Patent Application No. 21150834.6, filed on Jan. 11, 2021. These applications are hereby incorporated by reference herein.

FIELD OF THE INVENTION

The invention relates to a light generating system and to a luminaire comprising such light generating system.

BACKGROUND OF THE INVENTION

The use of UV-light for disinfection of surfaces is known in the art. WO2015/189615, for instance, describes a disinfection system comprising: a luminaire assembly for generating a UV-C output suitable for disinfecting a surface upon which the UV-C is incident; a control system for controlling the UV-C output of the luminaire assembly and a remote monitoring device in communication with the control system, wherein, in use, the remote monitoring device generates a measured UV-C intensity based upon the intensity of the UV-C output of the luminaire assembly detected by the remote monitoring device at the location of the remote monitoring device.

SUMMARY OF THE INVENTION

UV light has been used for disinfection for over 100 years. Wavelengths between about 190 nm and 300 nm may be strongly absorbed by nucleic acids, which may result in defects in an organism's genome. This may be desired for killing bacteria and viruses, but may also have undesired side effects for humans. Therefore the selection of wavelength of radiation, intensity of radiation and duration of irradiation may be limited in environments where people may reside such as offices, public transport, cinema's, restaurants, shops, etc., thus limiting the disinfection capacity. Especially in such environments, additional measures of disinfection may be advantageous to prevent the spread of bacteria and viruses such as influenza or novel (corona) viruses like COVID-19, SARS and MERS.

It appears desirable to produce systems, that provide alternative ways for air treatment, such as disinfection. Further, existing systems for disinfection may not easily be implemented in existing infrastructure, such as in existing buildings like offices, hospitality areas, etc. and/or may not easily be able to serve larger spaces. This may again increase the risk of contamination. Further, incorporation in HVAC systems may not lead to desirable effects and appears to be relatively complex. Further, existing systems may not be efficient, or may be relatively bulky, and may also not easily be incorporated in functional devices, such as e.g. luminaires.

Other disinfection systems may use one or more anti-microbial and/or anti-viral means to disinfect a space or an object. Examples of such means may be chemical agents which may raise concerns. For instance, the chemical agents may also be harmful for people and pets.

Hence, it is an aspect of the invention to provide an alternative light generating system, which preferably further at least partly obviates one or more of above-described drawbacks. The present invention as claimed in claim 1 may have as object to overcome or ameliorate at least one of the disadvantages of the prior art, or to provide a useful alternative.

Herein, in embodiments a light generating system is proposed which may have a lighting function as well as a disinfection function and/or air treatment function. These functions may be executed at the same time, may be executed partly overlapping in time, or may be executed in different time periods. Especially, the disinfection function or air treatment function may be provided by light having relatively small wavelengths, like wavelengths below 420 nm.

In embodiments, the disinfecting light, may especially comprise ultraviolet (UV) radiation, i.e., the second device light (see below) may comprise a wavelength selected from the ultraviolet wavelength range. However, other wavelengths are herein not excluded. The ultraviolet wavelength range is defined as light in a wavelength range from 100 to 380 nm and can be divided into different types of UV light/UV wavelength ranges (see Table 1). Different UV wavelengths of radiation may have different properties and thus may have different compatibility with human presence and may have different effects when used for disinfection (Table 1).

TABLE 1

Properties of different types of violet and UV wavelength light

| Name | Short name | Wavelength (nm) | (Relative) sterilization effectiveness | | Safe Radiation | Vitamin D generation | Ozone generation |
| --- | --- | --- | --- | --- | --- | --- | --- |
| | | | Bacteria | Viruses | | | |
| Violet | V | 380-420 | +/− | − | + | | |
| Ultra-violet A | UV-A | 315-380 | + | − | + | | |
| Ultra-violet B | UV-B | 280-315 | + | +/− | +/− | + | |
| Near ultraviolet C | Near UV-C | 230-280 | + | + | − | | |
| Far ultra-violet | Far UV | 190-230 | + | + | + | | +/− |

TABLE 1-continued

Properties of different types of violet and UV wavelength light

| Name | Short name | Wavelength (nm) | (Relative) sterilization effectiveness | | Safe Radiation | Vitamin D generation | Ozone generation |
| --- | --- | --- | --- | --- | --- | --- | --- |
| | | | Bacteria | Viruses | | | |
| Extreme ultraviolet C | Extreme UV-C | 100-190 | + | + | − | | + |

Each UV type/wavelength range may have different benefits and/or drawbacks. Relevant aspects may be (relative) sterilization effectiveness, safety (regarding radiation), and ozone production (as result of its radiation). Depending on an application a specific type of UV light or a specific combination of UV light types may be selected and provides superior performance over other types of UV light. UV-A may be (relatively) safe and may kill bacteria, but may be less effective in killing viruses. UV-B may be (relatively) safe when a low dose (i.e. low exposure time and/or low intensity) is used, may kill bacteria, and may be moderately effective in killing viruses. UV-B may also have the additional benefit that it can be used effectively in the production of vitamin D in a skin of a person or animal. Near UV-C may be relatively unsafe, but may effectively kill bacteria and viruses. Far UV may also be effective in killing bacteria and viruses, but may be (relatively to other UV-C wavelength ranges) (rather) safe. Far-UV light may generate some ozone which may be harmful for human beings and animals. Extreme UV-C may also be effective in killing bacteria and viruses, but may be relatively unsafe. Extreme UV-C may generate ozone which may be undesired when exposed to human beings or animals. In some application ozone may be desired and may contribute to disinfection, but then its shielding from humans and animals may be desired. Hence, in the table "+" for ozone production especially implies that ozone is produced which may be useful for disinfection applications, but may be harmful for humans/animals when they are exposed to it. Hence, in many applications this "+" may actually be undesired while in others, it may be desired.

Hence, in embodiments, the (second device) light may comprise a wavelength in the UV-A range. In further embodiments, the (second device) light may comprise a wavelength in the UV-B range. In further embodiments, the (second device) light may comprise a wavelength in the Near UV-C range. In further embodiments, the (second device) light may comprise a wavelength in the Far UV range. In further embodiments, the (second device) light may comprise a wavelength in the extreme UV-C range. The Near UV-C, the Far UV and the extreme UV-C ranges may herein also collectively be referred to as the UV-C range. Hence, in embodiments, the (second device) light may comprise a wavelength in the UV-C range. However, in other embodiments the wavelength may be selected from the range of 380-420 nm. Especially, the invention may use ultraviolet light (as second device light).

In an aspect, the invention provides a light generating system configured to provide system light (in a basic operational mode, also generally referred to as operational mode). Especially, the light generating system comprises (i) a first light generating device, (ii) a second light generating device, and (iii) a waveguide. In embodiments, the waveguide may have a first face, a second face, and a side face bridging the first face and the second face. Further, in embodiments, the first light generating device may be configured to generate first device light. Especially, in embodiments in an operational mode the first device light has a color point in the visible. Further, in embodiments the first light generating device is configured to irradiate the side face. Especially, in embodiments in an operational mode at least part of the first device light may escape from the waveguide via the first face. Further, in embodiments the second light generating device may be configured to generate second device light. Especially, in embodiments in an operational mode the second device light may have a centroid wavelength of at maximum 420 nm. Yet further, in embodiments in an operational mode the second device light may have a spectral power distribution differing from a spectral power distribution of the first device light. Further, in embodiments the second light generating device may be configured upstream of the second face. Especially, in embodiments in an operational mode at least part of the second device light may be transmitted through the waveguide and escapes from the waveguide via the first face. Therefore, in embodiments the invention provides a light generating system configured to provide system light, wherein the light generating system comprises (i) a first light generating device, (ii) a second light generating device, and (iii) a waveguide, wherein: (a) the waveguide has a first face, a second face, and a side face bridging the first face and the second face; (b) the first light generating device is configured to generate first device light, wherein in an operational mode the first device light has a color point in the visible; the first light generating device is configured to irradiate the side face, wherein in an operational mode at least part of the first device light escapes from the waveguide via the first face; and (c) the second light generating device is configured to generate second device light, wherein in an operational mode the second device light has a centroid wavelength of at maximum 420 nm, and has a spectral power distribution differing from a spectral power distribution of the first device light; the second light generating device is configured upstream of the second face; wherein in an operational mode at least part of the second device light is transmitted through the waveguide and escapes from the waveguide via the first face.

The expression "waveguide" in the application might be interpreted as relating to a waveguide plate comprising the first face, the second face, and the side face bridging the first face and the second face.

In yet an aspect, the invention provides a light generating system. Especially, the light generating system is configured to provide system light (in an operational mode. The light generating system may comprise a first light generating device. Further, in embodiments the light generating system may comprise a second light generating device. Yet further, in embodiments the light generating system may comprise a waveguide. Especially, in embodiments the waveguide has a first face and a second face. Yet further, in embodiments the waveguide may comprise a side face bridging the first face and the second face. In specific embodiments, the waveguide may comprise one or more first regions, comprising a first material having a first material composition, and one or more second regions, comprising a second material having a second material composition. In specific embodiments, the first material composition and the second material composition may differ. Especially, the first light generating device may be configured to generate first device light. In embodiments, in an operational mode the first device light has a color point in the visible. Especially, in embodiments the first light generating device may be configured to irradiate the side face, wherein in an operational mode at least part of the first device light escapes from the waveguide via the first face. Further, especially the second light generating device may be configured to generate second device light. In embodiments, in an operational mode the second device light may have a centroid wavelength of at maximum 420 nm. Especially, in embodiments the second light generating device may be configured upstream of at least one of the one or more second regions and may be configured upstream of the second face. Especially, in embodiments the second light generating device may be configured to irradiate at least part of the at least one of the one or more second regions. Further, in embodiments in an operational mode at least part of the second device light may be transmitted through the waveguide via the at least part of the at least one of the one or more second regions and may escape from the waveguide via the first face. Therefore, in specific embodiments the invention provides a light generating system configured to provide system light, wherein the light generating system comprises (i) a first light generating device, (ii) a second light generating device, and (iii) a waveguide, wherein: (a) the waveguide has a first face, a second face, and a side face bridging the first face and the second face; wherein the waveguide comprises one or more first regions, comprising a first material having a first material composition, and one or more second regions, comprising a second material having a second material composition, wherein the first material composition and the second material composition differ; (b) the first light generating device is configured to generate first device light, wherein in an operational mode the first device light has a color point in the visible; the first light generating device is configured to irradiate the side face, wherein in an operational mode at least part of the first device light escapes from the waveguide via the first face; and (c) the second light generating device is configured to generate second device light, wherein in an operational mode the second device light has a centroid wavelength of at maximum 420 nm; the second light generating device is configured upstream of at least one of the one or more second regions and configured upstream of the second face; wherein the second light generating device is configured to irradiate at least part of the at least one of the one or more second regions, wherein in an operational mode at least part of the second device light is transmitted through the waveguide via the at least part of the at least one of the one or more second regions and escapes from the waveguide via the first face.

With system(s) it is possible to generate visible light and light that may be used for e.g. disinfection or air treatment purposes. Further, the present invention may make use of a waveguide, which may allow desirable shapes and good light distributions. However, the present invention may also take account of the fact that waveguides may have lower transmission for shorter wavelengths. Hence, the present invention may provide an elegant and efficient solution for a system that may have a lighting and a disinfection and/or air treatment function.

As indicated above, the invention provides a light generating system. Especially, the light generating system is configured to provide system light. The system light may have a spectral power distribution. In embodiments, the spectral power distribution may be fixed and in yet other embodiments, the spectral power distribution (of the system light) may be controllable. Especially, in one or more operational modes the system light is visible light, such as white light. However, other embodiments may also be possible. See further below. Further, in embodiments the light generating system may be configured to provide functional radiation, which may have one or more of an air treatment function or a disinfection function. This functional radiation is herein also indicated as second device light.

Especially, in embodiments the light generating system comprises (i) a first light generating device, (ii) a second light generating device, and (iii) a waveguide. Herein, the term "first light generating device" may also refer to a plurality of (different) first light generating devices. Herein, the term "second light generating device" may also refer to a plurality of (different) second light generating devices. Here below, some aspects in relation to light generating devices in general are described.

A light generating device may comprise one or more light sources.

The term "light source" may in principle relate to any light source known in the art. It may be a conventional (tungsten) light bulb, a low pressure mercury lamp, a high pressure mercury lamp, a fluorescent lamp, a LED (light emissive diode). In a specific embodiment, the light source comprises a solid state LED light source (such as a LED or laser diode (or "diode laser")). The term "light source" may also relate to a plurality of light sources, such as 2-200 (solid state) LED light sources. Hence, the term LED may also refer to a plurality of LEDs. Further, the term "light source" may in embodiments also refer to a so-called chips-on-board (COB) light source. The term "COB" especially refers to LED chips in the form of a semiconductor chip that is neither encased nor connected but directly mounted onto a substrate, such as a PCB. Hence, a plurality of light semiconductor light source may be configured on the same substrate. In embodiments, a COB is a multi LED chip configured together as a single lighting module.

The light source has a light escape surface. Referring to conventional light sources such as light bulbs or fluorescent lamps, it may be outer surface of the glass or quartz envelope. For LED's it may for instance be the LED die, or when a resin is applied to the LED die, the outer surface of the resin. In principle, it may also be the terminal end of a fiber. The term escape surface especially relates to that part of the light source, where the light actually leaves or escapes from the light source. The light source is configured to provide a beam of light. This beam of light (thus) escapes form the light exit surface of the light source.

The term "light source" may refer to a semiconductor light-emitting device, such as a light emitting diode (LEDs), a resonant cavity light emitting diode (RCLED), a vertical cavity laser diode (VCSELs), an edge emitting laser, etc. . . . . The term "light source" may also refer to an organic light-emitting diode, such as a passive-matrix (PMOLED) or an active-matrix (AMOLED). In a specific embodiment, the light source comprises a solid-state light source (such as a LED or laser diode). In an embodiment, the light source comprises a LED (light emitting diode). The terms "light source" or "solid state light source" may also refer to a superluminescent diode (SLED).

The term LED may also refer to a plurality of LEDs. Further, the term "light source" may in embodiments also refer to a so-called chips-on-board (COB) light source. The term "COB" especially refers to LED chips in the form of a semiconductor chip that is neither encased nor connected but directly mounted onto a substrate, such as a PCB. Hence, a plurality of semiconductor light sources may be configured on the same substrate. In embodiments, a COB is a multi LED chip configured together as a single lighting module.

The term "light source" may also relate to a plurality of (essentially identical (or different)) light sources, such as 2-2000 solid state light sources. In embodiments, the light source may comprise one or more micro-optical elements (array of micro lenses) downstream of a single solid-state light source, such as a LED, or downstream of a plurality of solid-state light sources (i.e. e.g. shared by multiple LEDs). In embodiments, the light source may comprise a LED with on-chip optics. In embodiments, the light source comprises a pixelated single LEDs (with or without optics) (offering in embodiments on-chip beam steering).

In embodiments, the light source may be configured to provide primary radiation, which is used as such, such as e.g. a blue light source, like a blue LED, or a green light source, such as a green LED, and a red light source, such as a red LED. Such LEDs, which may not comprise a luminescent material ("phosphor") may be indicated as direct color LEDs.

In other embodiments, however, the light source may be configured to provide primary radiation and part of the primary radiation is converted into secondary radiation. Secondary radiation may be based on conversion by a luminescent material. The secondary radiation may therefore also be indicated as luminescent material radiation. The luminescent material may in embodiments be comprised by the light source, such as a LED with a luminescent material layer or dome comprising luminescent material. Such LEDs may be indicated as phosphor converted LEDs or PC LEDs. In other embodiments, the luminescent material may be configured at some distance ("remote") from the light source, such as a LED with a luminescent material layer not in physical contact with a die of the LED. Hence, in specific embodiments the light source may be a light source that during operation emits at least light at wavelength selected from the range of 380-470 nm. However, other wavelengths may also be possible. This light may partially be used by the luminescent material.

In embodiments, the light source may be selected from the group of laser diodes and superluminescent diodes.

The term "laser light source" especially refers to a laser. Such laser may especially be configured to generate laser light source light having one or more wavelengths in the UV, visible, or infrared, especially having a wavelength selected from the spectral wavelength range of 200-2000 nm, such as 300-1500 nm. The term "laser" especially refers to a device that emits light through a process of optical amplification based on the stimulated emission of electromagnetic radiation.

Especially, in embodiments the term "laser" may refer to a solid-state laser. In specific embodiments, the terms "laser" or "laser light source", or similar terms, refer to a laser diode (or diode laser).

Hence, in embodiments the light source comprises a laser light source. In embodiments, the terms "laser" or "solid state laser" may refer to one or more of cerium doped lithium strontium (or calcium) aluminum fluoride (Ce: LiSAF, Ce:LiCAF), chromium doped chrysoberyl (alexandrite) laser, chromium ZnSe (Cr:ZnSe) laser, divalent samarium doped calcium fluoride (Sm:CaF$_2$) laser, Er:YAG laser, erbium doped and erbium-ytterbium codoped glass lasers, F-Center laser, holmium YAG (Ho:YAG) laser, Nd:YAG laser, NdCrYAG laser, neodymium doped yttrium calcium oxoborate Nd:YCa$_4$O(BO$_3$)$_3$ or Nd:YCOB, neodymium doped yttrium orthovanadate (Nd:YVO$_4$) laser, neodymium glass (Nd:glass) laser, neodymium YLF (Nd: YLF) solid-state laser, promethium 147 doped phosphate glass (147Pm$^{3+}$:glass) solid-state laser, ruby laser (Al$_2$O$_3$: Cr$^{3+}$), thulium YAG (Tm:YAG) laser, titanium sapphire (Ti:sapphire; Al$_2$O$_3$:Ti$^{3+}$) laser, trivalent uranium doped calcium fluoride (U:CaF$_2$) solid-state laser, Ytterbium doped glass laser (rod, plate/chip, and fiber), Ytterbium YAG (Yb:YAG) laser, Yb$_2$O$_3$ (glass or ceramics) laser, etc.

In embodiments, the terms "laser" or "solid state laser" may refer to one or more of a semiconductor laser diode, such as GaN, InGaN, AlGaInP, AlGaAs, InGaAsP, lead salt, vertical cavity surface emitting laser (VCSEL), quantum cascade laser, hybrid silicon laser, etc.

A laser may be combined with an upconverter in order to arrive at shorter (laser) wavelengths. For instance, with some (trivalent) rare earth ions upconversion may be obtained or with non-linear crystals upconversion can be obtained. Alternatively, a laser can be combined with a downconverter, such as a dye laser, to arrive at longer (laser) wavelengths.

As can be derived from the below, the term "laser light source" may also refer to a plurality of (different or identical) laser light sources. In specific embodiments, the term "laser light source" may refer to a plurality N of (identical) laser light sources. In embodiments, N=2, or more. In specific embodiments, N may be at least 5, such as especially at least 8. In this way, a higher brightness may be obtained. In embodiments, laser light sources may be arranged in a laser bank (see also above). The laser bank may in embodiments comprise heat sinking and/or optics e.g. a lens to collimate the laser light.

The laser light source is configured to generate laser light source light (or "laser light"). The light source light may essentially consist of the laser light source light. The light source light may also comprise laser light source light of two or more (different or identical) laser light sources. For instance, the laser light source light of two or more (different or identical) laser light sources may be coupled into a light guide, to provide a single beam of light comprising the laser light source light of the two or more (different or identical) laser light sources. In specific embodiments, the light source light is thus especially collimated light source light. In yet further embodiments, the light source light is especially (collimated) laser light source light.

The phrases "different light sources" or "a plurality of different light sources", and similar phrases, may in embodiments refer to a plurality of solid-state light sources selected from at least two different bins. Likewise, the phrases "identical light sources" or "a plurality of same light sources", and similar phrases, may in embodiments refer to a plurality of solid-state light sources selected from the same bin.

The light source is especially configured to generate light source light having an optical axis (O), (a beam shape,) and a spectral power distribution. The light source light may in embodiments comprise one or more bands, having band widths as known for lasers. In specific embodiments, the band(s) may be relatively sharp line(s), such as having full width half maximum (FWHM) in the range of less than 20 nm at RT, such as equal to or less than 10 nm. Hence, the light source light has a spectral power distribution (intensity on an energy scale as function of the wavelength) which may comprise one or more (narrow) bands.

The beams (of light source light) may be focused or collimated beams of (laser) light source light. The term "focused" may especially refer to converging to a small spot. This small spot may be at the discrete converter region, or (slightly) upstream thereof or (slightly) downstream thereof. Especially, focusing and/or collimation may be such that the cross-sectional shape (perpendicular to the optical axis) of the beam at the discrete converter region (at the side face) is essentially not larger than the cross-section shape (perpendicular to the optical axis) of the discrete converter region (where the light source light irradiates the discrete converter region). Focusing may be executed with one or more optics, like (focusing) lenses. Especially, two lenses may be applied to focus the laser light source light. Collimation may be executed with one or more (other) optics, like collimation elements, such as lenses and/or parabolic mirrors. In embodiments, the beam of (laser) light source light may be relatively highly collimated, such as in embodiments ≤2° (FWHM), more especially ≤1° (FWHM), most especially ≤0.5° (FWHM). Hence, ≤2° (FWHM) may be considered (highly) collimated light source light. Optics may be used to provide (high) collimation (see also above).

In specific embodiments, the light generating device may comprise a plurality of different light sources, such as two or more subsets of light sources, with each subset comprising one or more light sources configured to generate light source light having essentially the same spectral power distribution, but wherein light sources of different subsets are configured to generate light source light having different spectral distributions. In such embodiments, a control system may be configured to control the plurality of light sources. In specific embodiments, the control system may control the subsets of light sources individually.

In embodiments, the light generating device may comprise a luminescent material. In embodiments, the light generating device may comprise a PC LED. In other embodiments, the light generating device may comprise a direct LED (i.e. no phosphor). In embodiments, the light generating device may comprise a laser device, like a laser diode. In embodiments, the light generating device may comprise a superluminescent diode.

In embodiments, the first light generating device may comprise two or more light generating devices, each selected from the above mentioned embodiments.

In embodiments, the second light generating device may comprise two or more light generating devices, each selected from the above mentioned embodiments.

In specific embodiments, the first light generating device may be configured to generate first device light, wherein in embodiments in an operational mode the first device light has a color point in the visible.

Especially, the first device light has a spectral power distribution. In embodiments, the spectral power distribution is fixed and may in specific embodiments e.g. only be controllable in intensity. In other embodiments, the spectral power distribution may be controllable. This may e.g. be the case in embodiments when the system comprises two or more different first light generating devices or when the spectral power distribution of a first light generating device as such is controllable. The latter may e.g. be the case when a first light generating system comprises two or more different (solid state) light sources, which are controllable. Hence, the first light generating device may at least be operated in an operational mode wherein the first device light has a color point in the visible. In specific embodiments, the first light generating device may at least be operated in an operational mode wherein the first device light is white light. Below, some aspects in relation to controlling and operational modes are discussed.

In specific embodiments, the second light generating device is configured to generate second device light, wherein in embodiments in an operational mode the second device light has a centroid wavelength of at maximum 420 nm.

Especially, the second device light has a spectral power distribution. In embodiments, the spectral power distribution is fixed and may in specific embodiments e.g. only be controllable in intensity. In other embodiments, the spectral power distribution may be controllable. This may e.g. be the case in embodiments when the system comprises two or more different second light generating devices or when the spectral power distribution of a second light generating device as such is controllable. The latter may e.g. be the case when a second light generating system comprises two or more different (solid state) light sources, which are controllable. Hence, the second light generating device may at least be operated in an operational mode wherein the first device light has a centroid wavelength of at maximum 420 nm.

In specific embodiments, the second light generating device may comprise one or more solid state light sources having peak wavelengths selected from the wavelength range of 190-420 nm, such as selected from the wavelength range of 250-420 nm. In further specific embodiments, the second light generating device may comprise one or more solid state light sources having peak wavelengths selected from the wavelength range of 190-380 nm, such as 250-370 nm.

Below, some aspects in relation to controlling and operational modes are discussed.

The term "centroid wavelength", also indicated as λc, is known in the art, and refers to the wavelength value where half of the light energy is at shorter and half the energy is at longer wavelengths; the value is stated in nanometers (nm). It is the wavelength that divides the integral of a spectral power distribution into two equal parts as expressed by the formula $\lambda c = \Sigma \lambda * I(\lambda)/(\Sigma I(\lambda)$, where the summation is over the wavelength range of interest, and $I(\lambda)$ is the spectral energy density (i.e. the integration of the product of the wavelength and the intensity over the emission band normalized to the integrated intensity). The centroid wavelength may e.g. be determined at operation conditions.

The waveguide may especially be used to spread the first device light over the waveguide, especially via total internal reflection (TIR), and outcoupling of at least part of the first device light from the waveguide. To this end, the waveguide may comprise one or more light outcoupling elements.

Instead of the term "waveguide" also the term "lightguide" may be applied.

The waveguide comprise light transmissive material. Hence, the waveguide comprises material that is optically transmissive.

The light transmissive material may comprise one or more materials selected from the group consisting of a transmissive organic material, such as selected from the group consisting of PE (polyethylene), PP (polypropylene), PEN (polyethylene naphthalate), PC (polycarbonate), polyurethanes (PU), polymethylacrylate (PMA), polymethylmethacrylate (PMMA) (Plexiglas or Perspex), polymethacrylimide (PMI), polymethylmethacrylimide (PMMI), styrene acrylonitrile resin (SAN), cellulose acetate butyrate (CAB), silicone, polyvinylchloride (PVC), polyethylene terephthalate (PET), including in an embodiment (PETG) (glycol modified polyethylene terephthalate), PDMS (polydimethylsiloxane), and COC (cyclo olefin copolymer). Especially, the light transmissive material may comprise an aromatic polyester, or a copolymer thereof, such as e.g. one or more of polycarbonate (PC), poly (methyl)methacrylate (P(M)MA), polyglycolide or polyglycolic acid (PGA), polylactic acid (PLA), polycaprolactone (PCL), polyethylene adipate (PEA), polyhydroxy alkanoate (PHA), polyhydroxy butyrate (PHB), poly(3-hydroxybutyrate-co-3-hydroxyvalerate) (PHBV), polyethylene terephthalate (PET), polybutylene terephthalate (PBT), polytrimethylene terephthalate (PTT), polyethylene naphthalate (PEN). Alternatively or additionally, one or more of polysulfone (PSU), polyethersulfone (PES) and polyphenylene sulfone (PPSU) may be applied. Hence, the light transmissive material is especially a polymeric light transmissive material.

However, in another embodiment the light transmissive material may comprise an inorganic material. Especially, the inorganic light transmissive material may be selected from the group consisting of glasses, (fused) quartz, transmissive ceramic materials, and silicones. Also hybrid materials, comprising both inorganic and organic parts may be applied. Especially, the light transmissive material comprises one or more of PMMA, transparent PC, or glass.

For instance, the light transmissive material may comprise a ceramic body, like a garnet type of material. In alterative embodiments, the light transmissive material may comprise an alumina material, such as an $Al_2O_3$ based material. In embodiments, the light transmissive material may comprise e.g. sapphire. Other materials may also be possible like one or more of $CaF_2$, MgO, $BaF_2$, $A_3B_5O_{12}$ garnet, ALON (aluminum oxynitride), $MgAl_2O_4$ and $MgF_2$.

The waveguide is especially in embodiments a body of light transmissive material.

The light transmissive material may have a relatively high (internal) transmission, and may in embodiments essentially transparent for the first device light.

Especially, the material has a light transmission in the range of 50-100%, especially in the range of 70-100%, for light having a wavelength selected from the visible wavelength range. Herein, the term "visible light" especially relates to light having a wavelength selected from the range of 380-780 nm.

The transmission (or light permeability) can be determined by providing light at a specific wavelength with a first intensity to the light transmissive material under perpendicular radiation and relating the intensity of the light at that wavelength measured after transmission through the material, to the first intensity of the light provided at that specific wavelength to the material (see also E-208 and E-406 of the CRC Handbook of Chemistry and Physics, 69th edition, 1088-1989).

In specific embodiments, a material may be considered transmissive when the transmission of the radiation at a wavelength or in a wavelength range, especially at a wavelength or in a wavelength range of radiation generated by a source of radiation as herein described, through a 1 mm thick layer of the material, especially even through a 5 mm thick layer of the material, under perpendicular irradiation with said radiation is at least about 20%, such as at least 40%, like at least 60%, such as especially at least 80%, such as at least about 85%, such as even at least about 90%.

The light transmissive material has light guiding or wave guiding properties. Hence, the light transmissive material is herein also indicated as waveguide material or light guide material. The light transmissive material will in general have (some) transmission of one or more of (N)UV, visible and (N)IR radiation, such as in embodiments at least visible light, in a direction perpendicular to the length of the light transmissive material. Without the activator (dopant) such as trivalent cerium, the internal transmission in the visible might be close to 100%.

The transmission of the light transmissive material (as such) for one or more luminescence wavelengths may be at least 80%/cm, such as at least 90%/cm, even more especially at least 95%/cm, such as at least 98%/cm, such as at least 99%/cm. This implies that e.g. a 1 $cm^3$ cubic shaped piece of light transmissive material, under perpendicular irradiation of radiation having a selected luminescence wavelength (such as a wavelength corresponding to an emission maximum of the luminescence of the luminescent material of the light transmissive material), will have a transmission of at least 95%.

Herein, values for transmission especially refer to transmission without taking into account Fresnel losses at interfaces (with e.g. air). Hence, the term "transmission" especially refers to the internal transmission. The internal transmission may e.g. be determined by measuring the transmission of two or more bodies having a different width over which the transmission is measured. Then, based on such measurements the contribution of Fresnel reflection losses and (consequently) the internal transmission can be determined. Hence, especially, the values for transmission indicated herein, disregard Fresnel losses.

In embodiments, an anti-reflection coating may be applied to the luminescent body, such as to suppress Fresnel reflection losses (during the light incoupling process).

In addition to a high transmission for the wavelength(s) of interest, also the scattering for the wavelength(s) may especially be low. Hence, the mean free path for the wavelength of interest only taking into account scattering effects (thus not taking into account possible absorption (which should be low anyhow in view of the high transmission), may be at least 0.5 times the length of the body, such as at least the length of the body, like at least twice the length of the body. For instance, in embodiments the mean free path only taking into account scattering effects may be at least 5 mm, such as at least 10 mm. The wavelength of interest may especially be the wavelength at maximum emission of the luminescence of the luminescent material. The term "mean free path" is especially the average distance a ray will travel before experiencing a scattering event that will change its propagation direction.

In embodiments, the element comprising the light transmissive material may essentially consist of the light transmissive material. In specific embodiments, the element comprising the light transmissive material may be a light transparent element.

Especially, the light transmissive element, such as the light transparent element, may in embodiments have an absorption length and/or a scatter length of at least the length (or thickness) of the light transmissive element, such as at least twice the length of the light transmissive element. The absorption length may be defined as the length over which the intensity of the light along a propagation direction due to absorption drops with 1/e. Likewise, the scatter length may be defined as the length along a propagation direction along which light is lost due to scattering and drops thereby with a factor 1/e. Here, the length may thus especially refer to the distance between a primary face and a secondary face of the light transmissive element, with the light transmissive material configured between the primary face and the secondary face.

In addition to the light transmissive material, the waveguide may comprise light outcoupling elements. This may include one or more of elements embedded by the light transmissive material, and elements at a face of the waveguide (such as at one or more of the first face and the second face, see also below).

The light outcouple elements may comprise particles embedded in the light transmissive material of the waveguide. Such particles may be scattering particles (like e.g. comprising one or more of $Al_2O_3$, $BaSO_4$ and $TiO_2$). The light outcouple elements may comprise elements at one or more faces of the waveguide, like indentations, scratches, grooves, dots of material, light scattering structures (in optical contact with one of the faces), etc. etc.

Light outcouple elements are for instance described in WO99₂68, WO2012059866, WO2018041470, and WO03027569, which are herein incorporated by reference. The light outcouple elements may be configured as regular pattern of light outcouple elements. The light outcouple elements may especially be configured to couple the first device light out from the waveguide, such that an intensity of the first device light may escape from the waveguide relatively evenly distributed over the waveguide.

In specific embodiments, the waveguide may have a first face, a second face, and a side face bridging the first face and the second face.

Especially, the waveguide may have the shape of a plate, having length, width, or diameter, which may essentially be larger than a height. Hence, the waveguide may have a first dimension, defined as a circular equivalent diameter, and a second dimension, perpendicular thereto, and especially defined as a height, wherein the first dimension may be at least 2 times, like at least 5, times, such as at least 10 times larger than the second dimension. Would the waveguide have a length and a width, each may be at least 2 times, like at least 5, times, such as at least 10 times larger than the height.

In embodiments, the circular equivalent diameter may be selected from the range of 0.1-2 m, more especially 0.2-1.5 m, most especially 0.3-1 m. Further, in embodiments, the height may be selected from the range of 0.1-3 cm, more especially 0.2-2 cm, most especially 0.3-1 cm.

In specific embodiments, the length may be selected from the range of 0.1-2 m, more especially 0.2-1.5 m, most especially 0.3-1 m. In specific embodiments, a width may be selected from the range of 0.1-2 m, more especially 0.2-1.5 m, most especially 0.3-1 m. In specific embodiments, the height may be selected from the range of 0.1-3 cm, more especially 0.2-2 cm, most especially 0.3-1 cm.

In embodiments, the waveguide may have a rectangular shape or a circular shape, or a hexagonal shape, or an octagonal shape. Especially, the waveguide may have a rectangular shape. However, other shapes may also be possible, such as rectangular with rounded corners, oval, etc. In specific embodiments rectangular may be square; in other embodiments rectangular may be non-square.

The equivalent circular diameter (or ECD) of an (irregularly shaped) two-dimensional shape is the diameter of a circle of equivalent area. For instance, the equivalent circular diameter of a square with side a is $2*a*SQRT(1/\pi)$. For a circle, the diameter is the same as the equivalent circular diameter. Would a circle in an xy-plane with a diameter D be distorted to any other shape (in the xy-plane), without changing the area size, than the equivalent circular diameter of that shape would be D.

As will be further elucidated below, the side face may especially be configured to receive first device light. Hence, in this respect the system may be an edge-lit system. However, the second light generating device may especially be configured to irradiate the second face.

When the waveguide has a circular shape, the side face may comprise a single side face. When the waveguide has a rectangular shape, the side face may comprise four side faces.

In embodiments, the waveguide may essentially consist of a single material (composition). In other embodiments, the waveguide may comprise two types of regions, each comprising different material (compositions). The latter embodiments are further described (in some embodiments) below.

Especially, the waveguide may comprise one or more first regions, comprising a first material having a first material composition, and one or more second regions, comprising a second material having a second material composition. Further, especially, the first material composition and the second material composition differ.

The waveguide may also comprise yet further regions. However, embodiments of the invention are amongst others described in relation to two types of regions.

For instance, the first material and the second material are different. Hence, their compositions may differ. In other embodiments, the first material may comprise one or more different materials, and the second material may comprise one or more different materials, and the material compositions of the first material and the second material may differ. For instance, in specific embodiments the first material and the second material may comprise one or more identical materials, but the compositions of the material compositions differ. In other embodiments, the first material composition and the second material composition differ at least in one material. The term "different material" may especially refer to chemically different materials. For instance, glass and quartz differ, glass and polymer differ, PC and PMMA differ, PET and PEN differ, silicone and glass differ, etc. etc.

In embodiments, the first material may be light transmissive for the first device light. The first material may also be light transmissive for the second device light. It may, however, be that in embodiments the transmission for the first device light is higher than for the second device light. In embodiments, the second material may be light transmissive for the second device light. The second material may also be light transmissive for the first device light.

In embodiments, the second material may be more flexible than the first material. In embodiments, the first material may be more rigid than the second material. Hence, in specific embodiments the first regions may be rigid and the second regions may be flexible.

Especially, in embodiments the first material may be available as main phase whereas the second material may be available as local spots (see also below).

In embodiments, the first regions may have a height identical to the height of the waveguide. Likewise, in embodiments the second regions may have a height identical to the height of the waveguide. Hence, in embodiments the first face may be defined by the first regions and second regions. Likewise, in embodiments the second face may be defined by the first regions and second regions. Hence, when the first regions encloses the one or more second regions, this especially refers to the fact that in the plane of the waveguide, the second regions are enclosed by the first regions. However, the first region(s) and the second region(s) may share the same first face and the same second face.

As also indicated above, especially, the first light generating device may be configured to irradiate the side face. Upon irradiation of the side face, at least part of the first device light may enter the waveguide, and propagate through the waveguide. At least part of the first device light that entered the waveguide may escape from the waveguide, e.g. due to the presence of outcouple elements. Hence, in an operational mode at least part of the first device light escapes from the waveguide via the first face.

Especially, at least part, such as at least 50% of the spectral power of the first device light that escapes from the waveguide, may do so only after at least one reflection within the waveguide. Even more especially, at least 60%, such as at least 80%, of the spectral power of the first device light that escapes from the waveguide, may do so only after at least one reflection within the waveguide. Yet, in embodiments at least 90% of the spectral power of the first device light that escapes from the waveguide, may do so only after at least one reflection within the waveguide.

In embodiments, the second light generating device may be configured upstream of at least one of the one or more second regions and configured upstream of the second face.

The terms "upstream" and "downstream" relate to an arrangement of items or features relative to the propagation of the light from a light generating means (here the especially the light source), wherein relative to a first position within a beam of light from the light generating means, a second position in the beam of light closer to the light generating means is "upstream", and a third position within the beam of light further away from the light generating means is "downstream".

Hence, whereas the first light generating device may primarily irradiate a side face (or edge face), the second light generating device may primarily irradiate the second face. More especially, the second light generating device may primarily irradiate a second region, and not a first region. Hence, in embodiments an optical axis of the first device light and an optical axis of the second device light have a mutual angle of about 90°. Especially, the optical axis may be defined as an imaginary line that defines the path along which light propagates through the system starting from the light generating element, here especially the light source.

Hence, in specific embodiments the second light generating device may be configured to irradiate at least part of the at least one of the one or more second regions, wherein in an operational mode at least part of the second device light is transmitted through the waveguide via the at least part of the at least one of the one or more second regions and escapes from the waveguide via the first face. In this way, a substantial part of, even more especially essentially all, second device light that escapes from the first face may escape from the second region. Hence, the second device light may in embodiments substantially not propagate through the first material, but only through the second material, when it propagates from the second face to the first face.

Especially, at maximum 30% of the spectral power of the second device light that escapes from the waveguide, may do so only after at least one reflection within the waveguide, like at maximum 20%, such as at maximum 10%.

In specific embodiments, the majority of the first device light (especially ≥70%, more especially ≥80%, most especially ≥90%) may be guided in the lightguide via TIR before exiting. In specific embodiments, the majority of the second device light (especially ≥70%, more especially ≥80%, most especially ≥90%) may not be guided in the lightguide. In specific embodiments, the majority of the first device light (especially ≥70%, more especially ≥80%, most especially ≥90%) may exit at the one or more first regions. In specific embodiments, the majority of the second device light (especially ≥70%, more especially ≥80%, most especially ≥90%) may exit at the one or more second regions. In specific embodiments, the average path length of the first device light may be at least two (more especially at least 3, most especially at least 4) times longer in the light guide than the second device light.

Here below, some further embodiments are described.

As indicated above, the waveguide may comprise one or more first regions and one or more second regions. Especially, in embodiments the one or more first regions and the one or more second regions defined the waveguide. In specific embodiments, the one or more first regions define a first volume $V_1$ and the one or more second regions define a second volume $V_2$. As indicated above, in specific embodiments a total volume of the waveguide may be $V_w$, which may be $V_1+V_2$.

In embodiments, $0.001 \leq V_2/V_1 \leq 5$, even more especially $0.001 \leq V_2/V_1 \leq 1$. In specific embodiments, the first volume may be larger than the second volume. Hence, in specific embodiments $V_2 \leq V_1$. For instance, in embodiments $V_2/V_1 \leq 0.75$. Even more especially, the second volume is in the order of at least about 1% of the first volume. Hence, in embodiments $0.01 \leq V_2/V_1$. Even more especially, in embodiments $0.01 \leq V_2/V_1 \leq 0.75$. For instance, in embodiments $0.01 \leq V_2/V_1 \leq 0.25$, such as $0.01 \leq V_2/V_1 \leq 0.1$. A large first volume may facilitate propagation of the first device light through the waveguide. A large second volume may allow a relative high intensity and/or even distribution of the second device light.

Further, it may be desirable that the index of refraction of the first material and the second material do not differ too much. A large difference may lead to a shorter propagation length of the first device light through the waveguide and/or may complicate the controllability of the outcoupling of the first device light. In specific embodiments, the first material has a first index of refraction $n_1$ and the second material has a second index of refraction $n_2$. Especially, in embodiments $0.9 \leq n_2/n_1 \leq 1.1$, such as in specific embodiments $0.95 \leq n_2/n_1 \leq 1.05$.

By using different materials or material compositions, the transmission of the one or more second regions may be optimized for the second device light and/or the transmission for the one or more first regions may be optimized for the first device light. alternatively or additionally, by using different materials or material compositions, one may optimize material properties, also in view of the fact that in embodiments the one or more second regions may e.g. be a second phase in an essentially first phase comprising the one (or more first) region(s). In this way, one may take account of one or more of optical aspects, material aspects, and also material processing aspects. For instance, the waveguide may be provided via 3D printing, 2K (injection) molding, two component extrusion, filling a plate of first material with holes with the second material, filing a mold with second regions with the first material, providing the first regions and subsequently the second regions e.g. filling gaps in the first regions e.g. using dispensing, etc. etc. In specific embodiments, the waveguide may comprise a waveguide plate comprising the first face, the second face, and the side face bridging the first face and the second face; and the waveguide plate comprise a plate of the first material (such as e.g.

one or more of PC and PMMA) having through holes filled with the second material (such as e.g. silicone).

For instance, a material that may have a relatively good transmission for the second device light may be less suitable as plate material or other continuous phase. With the present invention, different materials may be chosen for different purposes. Especially, both the first material and the second material are transmissive for the first device light, and the second material may also be light transmissive for the second device light.

In specific embodiments, the second material has a higher transmission for the second light than the first material. For instance, the second material may have an at least 5%, such an at least 10%, higher transmission for the second light than the first material. In specific embodiments, the second material has a 15% higher transmission for the second light than the first material. In other embodiments, the transmission of the second material for the second light may be smaller than 50%, and the transmission of the second material for the second light may be higher than 50%. For instance, in embodiments, the transmission of the second material for the second light may be smaller than 40%, and the transmission of the second material for the second light may be higher than 50%. Especially, in embodiments the transmission of the second material for the second light may be smaller than 30%, such as smaller than 20%, and the transmission of the second material for the second light may be higher than 50%. Here, e.g. transmission may be compared by using a 1 cm$^3$ cubic shaped piece of the respective light transmissive material, under perpendicular irradiation of (respective) radiation, and comparing the transmissions.

In specific embodiments, the first material may comprise one or more of PMMA, PET, PSU, PS and PC. Also blends of two or more polymeric materials may be applied as first material, such as e.g. PMMA-PC blends or copolymers of PMMA-PC. PMMA is an economical alternative to polycarbonate (PC) when tensile strength, flexural strength, transparency, polishability, and UV tolerance are more important than impact strength, chemical resistance, and heat resistance. Further, in specific embodiments, the second material may comprise one or more of glass, quartz, ceramic, and a silicone. Hence, also blends or mixtures of two or more second material may be applied. Silicone may be provided with a relatively high UV transmission and may be relatively easily formable. Hence, in specific embodiments the first material may comprise one or more of PMMA and PC; and the second material may comprise one or more of glass, quartz, ceramic, and a silicone.

Especially, at least part of the wavelengths of the spectral power distribution of the second device light may not be in the visible, but may have lower wavelengths. Hence, in specific embodiments, in an operational mode, the second device light has a centroid wavelength of at maximum 380 nm. For instance, the second light generating device may comprise one or more solid state light sources having peak wavelengths in the wavelength range of 190-380 nm, like selected from the range of 250-380 nm, such as 250-370 nm.

Hence, in embodiments, the second light generating device comprises a solid state light source, and wherein in an operational mode the second device light (or second device radiation) has a centroid wavelength of at maximum 380 nm.

Further, especially, in embodiments in an operational mode the first device light is visible light, having a color point in the visible, such as having a centroid wavelength selected from the range of 380-780 nm, even more especially selected from the range of 430-780 nm, such as selected from the range of 430-750 nm. In embodiments in an operational mode the first device light may have a centroid wavelength of at least 430 nm.

As indicated above, the system may especially be configured to generate system light. In embodiments, the system light may in an operational mode be visible light, such as in specific embodiments white light. Especially, the system light is visible light.

Several embodiments may be possible.

In embodiments the first device light and the second device light may be provided at the same time. In such embodiments, the system light may partly be based on the second device light would such second device light have wavelengths in the visible. Would the second device light essentially only have wavelengths external from the visible wavelength range, it may essentially not contribute to the optical properties in the visible of the system light, such as color point, correlated color temperature, etc.

Hence, in embodiments the system light may comprise first device light and second device light, whereby the system may at the same time may provide system light and functional light, whereby the latter may at least partly be a constituent of the system light. The term "functional light" refers to the second device light which may have an air treatment function and/or a disinfection function. For instance, assuming second device light having a peak wavelength of 405 nm, the system light may be white light comprising both the first device light and the second device light. Such system light may also have the function of air treatment and/or a disinfection.

The above may in fact still apply would the first device light and the second device light not be provided at the same time, but would they be provided with frequencies of at least about 50 Hz, such as at least about 60 Hz.

In embodiments the first device light and the second device light may be provided at different times. In such embodiments, the system light may essentially be based on the first device light. During time periods the system light would not be provided, the functional light may be provided, which may or may not have wavelengths in the visible.

Note that in embodiments there may also be a partial overlap in time.

In specific embodiments, the system light may essentially be provided by the first device light.

In embodiments in an operational mode at least 90% of a spectral power of the system light in the 380-780 nm wavelength range may be defined by the first device light. For instance, in embodiments in an operational mode the system light is white light, wherein at least 90% of a spectral power of the system light in the 380-780 nm wavelength range is defined by the first device light. More especially, in an operational mode at least 95%, such as at least 99%, of a spectral power of the system light in the 380-780 nm wavelength range is defined by the first device light.

The term "white light" herein, is known to the person skilled in the art. It especially relates to light having a correlated color temperature (CCT) between about 1800 K and 20000 K, such as between 2000 and 20000 K, especially 2700-20000 K, for general lighting especially in the range of about 2700 K and 6500 K. In embodiments, for backlighting purposes the correlated color temperature (CCT) may especially be in the range of about 7000 K and 20000 K. Yet further, in embodiments the correlated color temperature (CCT) is especially within about 15 SDCM (standard deviation of color matching) from the BBL (black body locus), especially within about 10 SDCM from the BBL, even more especially within about 5 SDCM from the BBL.

As indicated above, in embodiments the first device light and the second device light may in embodiments be provided during the same time, during overlapping times, or during separate periods. With the latter, it is especially referred to embodiments wherein the second device light essentially does not contribute to the visible system but is essentially only used as functional light, such as for air treatment and/or disinfection.

Hence, in specific embodiments the light generating system may be configured to provide in a further first operational mode first device light and no second device light, and in a further second operational mode, not or partly overlapping in time with the further first operational mode, second device light and no first device light. Especially, in embodiments the light generating system may be configured to provide in a further first operational mode first device light and no second device light, and in a further second operational mode, not overlapping in time with the further first operational mode, second device light and no first device light.

Hence, in embodiments in an operational mode the first device light and the second device light may be provided simultaneously. In alternative embodiments, in a further first and second operational mode the first device light and the second device light may be provided sequentially. In yet alternative embodiments, in a further first and second operational mode the first device light and the second device light may be provided partly overlapping in time.

In embodiments, in an operational mode the first device light has a first spectral power distribution and in an operational mode the second device light has a second spectral power distribution. In embodiments, the first spectral power distribution and the second spectral power distribution are differing. Especially, in embodiments in an operational mode the first device light has a first centroid wavelength $\lambda_{c,1}$, and the second device light has in an operational mode a second centroid wavelength $\lambda_{c,2}$. Especially, in embodiments $\lambda_{c,1}-\lambda_{c,2} \geq 20$ nm. Even more especially, $\lambda_{c,1}-\lambda_{c,2} \geq 40$ nm. Yet, in embodiments, $\lambda_{c,1}-\lambda_{c,2} \geq 50$ nm, such as at least 75 nm. Hence, the second device light may have a spectral power distribution differing from a spectral power distribution of the first device light.

Hence, in specific embodiments in an operational mode the first device light and the second device light may be provided simultaneously, and $\lambda_{c,1}-\lambda_{c,2} \geq 40$ nm. In alternative specific embodiments, in a sequential further first and second operational mode the first device light and the second device light may be provided sequentially $\lambda_{c,1}-\lambda_{c,2} \geq 40$ nm. In yet alternative specific embodiments, in a combined further first and second operational mode the first device light and the second device light may be provided partly overlapping in time $\lambda_{c,1}-\lambda_{c,2} \geq 40$ nm. Especially, in embodiments $\lambda_{c,2} \leq 410$ nm, such as in specific embodiments $\lambda_{c,2} \leq 405$ nm. In yet further specific embodiments, $\lambda_{c,2} \leq 400$ nm, such as $\lambda_{c,2} \leq 380$ nm.

The first device light and the second device light may be controlled. Controlling may imply one or more of controlling a color point of the first device light, controlling a correlated color temperature of the first device light, controlling an intensity of the first device light, controlling frequency of the first device light, controlling timing of the first device light, controlling a color point of the second device light, controlling an intensity of the second device light, controlling frequency of the second device light, controlling timing of the second device light, controlling a color point of the system light, controlling a correlated color temperature of the system light, controlling an intensity of the system light, controlling frequency of the system light, and controlling timing of the system light.

To this end, the light generating system may comprise a control system or may be functionally coupled to a control system.

The term "controlling" and similar terms especially refer at least to determining the behavior or supervising the running of an element. Hence, herein "controlling" and similar terms may e.g. refer to imposing behavior to the element (determining the behavior or supervising the running of an element), etc., such as e.g. measuring, displaying, actuating, opening, shifting, changing temperature, etc. Beyond that, the term "controlling" and similar terms may additionally include monitoring. Hence, the term "controlling" and similar terms may include imposing behavior on an element and also imposing behavior on an element and monitoring the element. The controlling of the element can be done with a control system, which may also be indicated as "controller". The control system and the element may thus at least temporarily, or permanently, functionally be coupled. The element may comprise the control system. In embodiments, the control system and element may not be physically coupled. Control can be done via wired and/or wireless control. The term "control system" may also refer to a plurality of different control systems, which especially are functionally coupled, and of which e.g. one control system may be a master control system and one or more others may be slave control systems. A control system may comprise or may be functionally coupled to a user interface.

The control system may also be configured to receive and execute instructions form a remote control. In embodiments, the control system may be controlled via an App on a device, such as a portable device, like a Smartphone or I-phone, a tablet, etc. The device is thus not necessarily coupled to the lighting system, but may be (temporarily) functionally coupled to the lighting system.

Hence, in embodiments the control system may (also) be configured to be controlled by an App on a remote device. In such embodiments the control system of the lighting system may be a slave control system or control in a slave mode. For instance, the lighting system may be identifiable with a code, especially a unique code for the respective lighting system. The control system of the lighting system may be configured to be controlled by an external control system which has access to the lighting system on the basis of knowledge (input by a user interface of with an optical sensor (e.g. QR code reader) of the (unique) code. The lighting system may also comprise means for communicating with other systems or devices, such as on the basis of Bluetooth, WIFI, LiFi, ZigBee, BLE or WiMAX, or another wireless technology.

The system, or apparatus, or device may execute an action in a "mode" or "operation mode" or "mode of operation" or "operational mode". Likewise, in a method an action or stage, or step may be executed in a "mode" or "operation mode" or "mode of operation" or "operational mode". This does not exclude that the system, or apparatus, or device may also be adapted for providing another controlling mode, or a plurality of other controlling modes. Likewise, this may not exclude that before executing the mode and/or after executing the mode one or more other modes may be executed.

However, in embodiments a control system may be available, that is adapted to provide at least the controlling mode. Would other modes be available, the choice of such modes may especially be executed via a user interface, though other options, like executing a mode in dependence of a sensor signal or a (time) scheme, may also be possible. The operation mode may in embodiments also refer to a system, or apparatus, or device, that can only operate in a single operation mode (i.e. "on", without further tunability).

Hence, in embodiments, the control system may control in dependence of one or more of an input signal of a user interface, a sensor signal (of a sensor), and a timer. The term "timer" may refer to a clock and/or a predetermined time scheme.

As indicated above, in embodiments the system may further comprise a control system, wherein the control system may especially be configured to control one or more of the first light generating device and the second light generating device, in embodiments in dependence of one or more of a user interface, a sensor, and a timer. Especially, the first light generating device and the second light generating device may be controlled individually. Especially, the timer may comprise in embodiments a time scheme. In embodiments, the control system may control one or more of the first light generating device and the second light generating device, in embodiments in dependence of a clock module (or timer). The clock module may provide a time scheme. The control system, especially in combination with the sensor, may provide the system with instructions for changing from a basic operational mode to a further first operational mode to a further second operational mode, depending on signals from the sensor. In embodiments, the control system may receive signals from a user interface, such that a user can control one or more of (i) potential on the first electrode, (ii) potential on the second electrode, and (iii) first volumetric flow rate, and (iv) second volumetric flow rate.

In embodiments, the sensor may comprise one or more sensors selected from the group comprising: a movement sensor, a presence sensor, a distance sensor, an ion sensor, a gas sensor, a virus sensor, an airflow sensor, a radiation sensor, a bacterium sensor, and a communication receiver.

Hence, the light generating system may in embodiments further comprise one or more (different) sensors. The sensor(s) may be functionally coupled to the control system.

In embodiments, the spectral power distribution of the first device light may be controlled. In embodiments, the spectral power distribution of the second device light may be controlled.

In embodiments, the spectral power distribution of the system light may be controlled. In embodiments, this may be due to the fact of one or more of (i) first light generating devices having different spectral power distributions, and (ii) a contribution of the second device light to the system light, wherein the contributions of the first device light and the second device light may be controlled.

The waveguide plate may comprise one or more second regions. In specific embodiments, the waveguide may comprise a single first region and N second regions enclosed by the first region. In embodiments, N=1. In yet further embodiments, N>1. When N>, the second regions may be distributed evenly or unevenly. In embodiments, an uneven distribution may facilitate a homogeneous outcoupling of the first device light. In specific embodiments, the second regions of the plurality of second regions may be homogenously distributed over the waveguide.

Especially, in embodiments N may be at least 3, such as N is at least 4. In yet further embodiments, N may be at least 5, for instance 6 or 9. Especially, in embodiments N≤20. More especially, in embodiments N≤15, such as N≤12.

In yet embodiments, the number of second regions may be at least 1 per 25 cm$^2$ waveguide, such as at least 1 per 16 cm$^2$ waveguide. Here, it is referred to the cross-sectional plate area $A_p$ of the waveguide plate.

With larger number of second regions, it may be easier to obtain a homogeneous beam of the second device light. Further, multiple small second regions may be less visible and may have less impact on the distribution of the first device light. A small number of second regions may in embodiments easier to produce.

Especially, in embodiments each of the one or more second regions may have a second region area $A_2$ in a plane of the waveguide plate, wherein the waveguide plate has a cross-sectional plate area $A_p$. In embodiments, $0.0001 \leq A_2/A_p$, such as $0.001 \leq A_2/A_p$, like in specific embodiments $0.001 \leq A_2/A_p$. Further, in specific embodiments $A_2/A_p \leq 0.2$, such as about $A_2/A_p \leq 0.1$ Hence, in embodiments $0.0001 \leq A_2/A_p \leq 0.2$, such as $0.0001 \leq A_2/A_p \leq 0.1$. In other embodiments, $0.001 \leq A_2/A_p \leq 0.2$, such as $0.01 \leq A_2/A_p \leq 0.2$, like $0.01 \leq A_2/A_p \leq 0.1$.

When there are a plurality of second regions, there may also especially be a plurality of second light generating device. Each light generating device may be configured to irradiate a single second region, though it is not excluded that two or more irradiate the same second region (at the second face). Hence, in embodiments the plurality of second light generating devices and the plurality of second regions may be aligned.

In specific embodiments, the waveguide may have a central part, wherein at least one of the one or more second regions at least partly coincide with the central part.

As indicated above, the waveguide may comprise light outcoupling structures. In specific embodiments, the one or more of the first face and the second face may comprise light outcouple structures.

In embodiments, the second face comprises light outcoupling structures. In yet further specific embodiments, only the second face comprises light outcoupling structures (and not the first face).

In embodiments, the light outcoupling structures are at least comprised by the one or more first regions. In further specific embodiments, only the one or more first regions comprise light outcoupling structures (and not the one or more second regions. In alternative embodiments, the one or more first regions and the one or more second regions may comprise light outcoupling structures.

In yet further specific embodiments, a density of light outcoupling structures may be homogeneous over the waveguide or may inhomogeneously be distributed over the waveguide.

In embodiments, the light outcoupling structures may especially be reflective for at least the first device light.

In embodiments, the light outcoupling structures are provided as a pattern, such as a pattern, such as a dot pattern, on the first face or the second face. The (dot) pattern may have a gradient.

In embodiments, the light outcoupling structures comprise one or more of $Al_2O_3$, $BaSO_4$ and $TiO_2$.

In embodiments, the light outcoupling structures comprise particulate material, such as particles of one or more of $Al_2O_3$, $BaSO_4$ and $TiO_2$. In such embodiments, the light outcoupling structures may in specific embodiments only be available in the one or more first regions, but in other embodiments also in the one or more second regions.

The light outcoupling structures may be relatively small, such as having dimensions equal to or smaller than 5 mm, such as especially smaller than 2 mm. In further specific embodiments, the light outcoupling structures may have dimensions equal to or smaller than 2 mm, such as equal to or smaller than 1 mm. The smaller the light outcoupling structures, the more homogenous the first device light may escape from the waveguide.

In embodiments, downstream of the waveguide, a diffusor may be configured. Hence, in embodiments the light generating system may further comprise a diffuser configured downstream of the first face, and configured to diffuse one or more of the first device light and the second device light. Especially, both may be diffused. In this way, a homogeneous distribution of first device light and/or second device light may be provided.

In embodiments, at the side of the second face, a reflector may be configured. In this way, first device light that may escape from the second face, may be reflected back into the waveguide, and may have another chance to escape from the waveguide via the first face. Hence, in embodiments the light generating system may further comprise a reflector configured at a side of the second face. The reflector may especially be reflective for first device light, though in embodiments the reflector may also be reflective for second device light. The reflector may be diffuse reflective or specular reflective, especially diffuse reflective (for the first device light). With a diffuse reflector, a homogeneous distribution of the outcoupled first device light may be facilitated.

The light generating system may be part of or may be applied in e.g. office lighting systems, household application systems, shop lighting systems, home lighting systems, accent lighting systems, spot lighting systems, theater lighting systems, fiber-optics application systems, projection systems, self-lit display systems, pixelated display systems, segmented display systems, warning sign systems, medical lighting application systems, indicator sign systems, decorative lighting systems, portable systems, automotive applications, (outdoor) road lighting systems, urban lighting systems, green house lighting systems, horticulture lighting, digital projection, or LCD backlighting. The light generating system (or luminaire) may be part of or may be applied in e.g. optical communication systems or disinfection systems.

The terms "visible", "visible light" or "visible emission" and similar terms refer to light having one or more wavelengths in the range of about 380-780 nm. Herein, UV may especially refer to a wavelength selected from the range of 200-380 nm.

The terms "light" and "radiation" are herein interchangeably used, unless clear from the context that the term "light" only refers to visible light. The terms "light" and "radiation" may thus refer to UV radiation, visible light, and IR radiation. In specific embodiments, especially for lighting applications, the terms "light" and "radiation" refer to (at least) visible light.

The terms "violet light" or "violet emission" especially relates to light having a wavelength in the range of about 380-440 nm. The terms "blue light" or "blue emission" especially relates to light having a wavelength in the range of about 440-495 nm (including some violet and cyan hues). The terms "green light" or "green emission" especially relate to light having a wavelength in the range of about 495-570 nm. The terms "yellow light" or "yellow emission" especially relate to light having a wavelength in the range of about 570-590 nm. The terms "orange light" or "orange emission" especially relate to light having a wavelength in the range of about 590-620 nm. The terms "red light" or "red emission" especially relate to light having a wavelength in the range of about 620-780 nm. The term "pink light" or "pink emission" refers to light having a blue and a red component. The term "cyan" may refer to one or more wavelengths selected from the range of about 490-520 nm. The term "amber" may refer to one or more wavelengths selected from the range of about 585-605 nm, such as about 590-600 nm.

In yet a further aspect, the invention also provides a lamp or a luminaire comprising the light generating system as defined herein. The luminaire may further comprise a housing, optical elements, louvres, etc. etc. . . . . The lamp or luminaire may further comprise a housing enclosing the light generating system. The lamp or luminaire may comprise a light window in the housing or a housing opening, through which the system light may escape from the housing. In yet a further aspect, the invention also provides a projection device comprising the light generating system as defined herein. Especially, a projection device or "projector" or "image projector" may be an optical device that projects an image (or moving images) onto a surface, such as e.g. a projection screen. The projection device may include one or more light generating systems such as described herein. Hence, in an aspect the invention also provides a light generating device selected from the group of a lamp, a luminaire, a projector device, a disinfection device, and an optical wireless communication device, comprising the light generating system as defined herein.

The light generating device may comprise a housing or a carrier, configured to house or support, respectively one or more of the first light generating device, the second light generating device, and the waveguide.

Instead of the terms "lighting device" or "lighting system", and similar terms, also the terms "light generating device" or "light generating system", (and similar terms), may be applied. A lighting device or a lighting system may be configured to generate device light (or "lighting device light") or system light ("or lighting system light").

The terms "light" and "radiation" are herein interchangeably used, unless clear from the context that the term "light" only refers to visible light. The terms "light" and "radiation" may thus refer to UV radiation, visible light, and IR radiation. In specific embodiments, especially for lighting applications, the terms "light" and "radiation" refer to visible light.

The term UV radiation may in specific embodiments refer to near UV radiation (NUV). Therefore, herein also the term "(N)UV" is applied, to refer to in general UV, and in specific embodiments to NUV. The term IR radiation may in specific embodiments refer to near IR radiation (NIR). Therefore, herein also the term "(N)IR" is applied, to refer to in general IR, and in specific embodiments to NIR.

Herein, the term "visible light" especially relates to light having a wavelength selected from the range of 380-780 nm.

Herein, UV (ultraviolet) may especially refer to a wavelength selected from the range of 190-380 nm, though in specific embodiments other wavelengths may also be possible.

Herein, IR (infrared) may especially refer to radiation having a wavelength selected from the range of 780-3000 nm, such as 780-2000 nm, e.g. a wavelength up to about 1500 nm, like a wavelength of at least 900 nm, though in specific embodiments other wavelengths may also be possible. Hence, the term IR may herein refer to one or more of near infrared (NIR (or IR-A)) and short-wavelength infrared (SWIR (or IR-B)), especially NIR.

Hence, in an aspect the invention provides a light generating system configured to provide system light, wherein the light generating system comprises (i) a first light generating device, (ii) a second light generating device, and (iii) a waveguide, wherein: (a) the waveguide has a first face, a second face, and a side face bridging the first face and the second face; wherein the waveguide comprises one or more first regions, comprising a first material having a first material composition, and one or more second regions, comprising a second material having a second material composition, wherein the first material composition and the second material composition differ; (b) the first light generating device is configured to generate first device light, wherein in an operational mode the first device light has a color point in the visible; the first light generating device is configured to irradiate the side face, wherein in an operational mode at least part of the first device light escapes from the waveguide via the first face; and (c) the second light generating device is configured to generate second device light, wherein in an operational mode the second device light has a centroid wavelength of at maximum 420 nm; the second light generating device is configured upstream of at least one of the one or more second regions and configured upstream of the second face; wherein the second light generating device is configured to irradiate at least part of the at least one of the one or more second regions, wherein in an operational mode at least part of the second device light is transmitted through the waveguide via the at least part of the at least one of the one or more second regions and escapes from the waveguide via the first face.

In such embodiments, in an operational mode at least part of the second device light may be transmitted through the waveguide essentially only via the at least part of the at least one of the one or more second regions and escapes from the waveguide via the first face; hence, without necessarily being guided/transmitted through the first region(s) of first material.

In specific embodiments, the waveguide may comprise a single first region and no second regions. In such embodiments, the waveguide may essentially consist of a single first material (having a first material composition). Hence, in such embodiments the transmission of second device light through the waveguide may essentially the same over the entire waveguide. Hence, in embodiments the first region may have a height identical to the height of the waveguide. In embodiments the first face may be defined by the first region. Likewise, in embodiments the second face may be defined by the first region. In embodiments wherein the waveguide may comprise only a first region (and no second regions), the first material may be selected from any of the above-mentioned materials. Hence, the first material for the waveguide essentially consisting of a single first region may in embodiments be selected from the materials defined above in relation to the first material and the second material. Therefore, in embodiments the second region(s) may extend from the first face to the second face of the waveguide and the first region(s) may extend from the first face to the second face of the waveguide.

Hence, in an aspect the invention provides a light generating system configured to provide system light, wherein the light generating system comprises (i) a first light generating device, (ii) a second light generating device, and (iii) a waveguide, wherein: (a) the waveguide has a first face, a second face, and a side face bridging the first face and the second face; (b) the first light generating device is configured to generate first device light, wherein in an operational mode the first device light has a color point in the visible; the first light generating device is configured to irradiate the side face, wherein in an operational mode at least part of the first device light escapes from the waveguide via the first face; and (c) the second light generating device is configured to generate second device light, wherein in an operational mode the second device light has a centroid wavelength of at maximum 420 nm, the second light generating device is configured upstream of the second face; wherein in an operational mode at least part of the second device light is transmitted through the waveguide and escapes from the waveguide via the first face. Especially, the second device light has in an operational mode a spectral power distribution differing from a spectral power distribution of the first device light. Essentially all embodiments described above in relation to the first region may also apply to the embodiments wherein the waveguide essentially consists of a single first region. In such embodiments, the first device light is configured to edge-lit the waveguide and the second device light is configured to irradiate the second face. Both the first device light and second device light may escape from the first face (in embodiments sequentially and/or simultaneously). Further, in such embodiments the second device light may of course substantially propagate through the first material (as there may be only a single first region).

In embodiments where there may be only a single (first) regions, V W may essentially be the same as $V_1$.

When there are first and second regions, substantially all second device light may propagate via only the one or more second regions from the second face to the first face, and escape from the first face. Hence, the second device may essentially not be configured upstream of a first region when there are also one or more second regions. Of course, when there is a single first region, the second device will also be configured upstream of the single first region.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE EMBODIMENTS

Figure 1A:
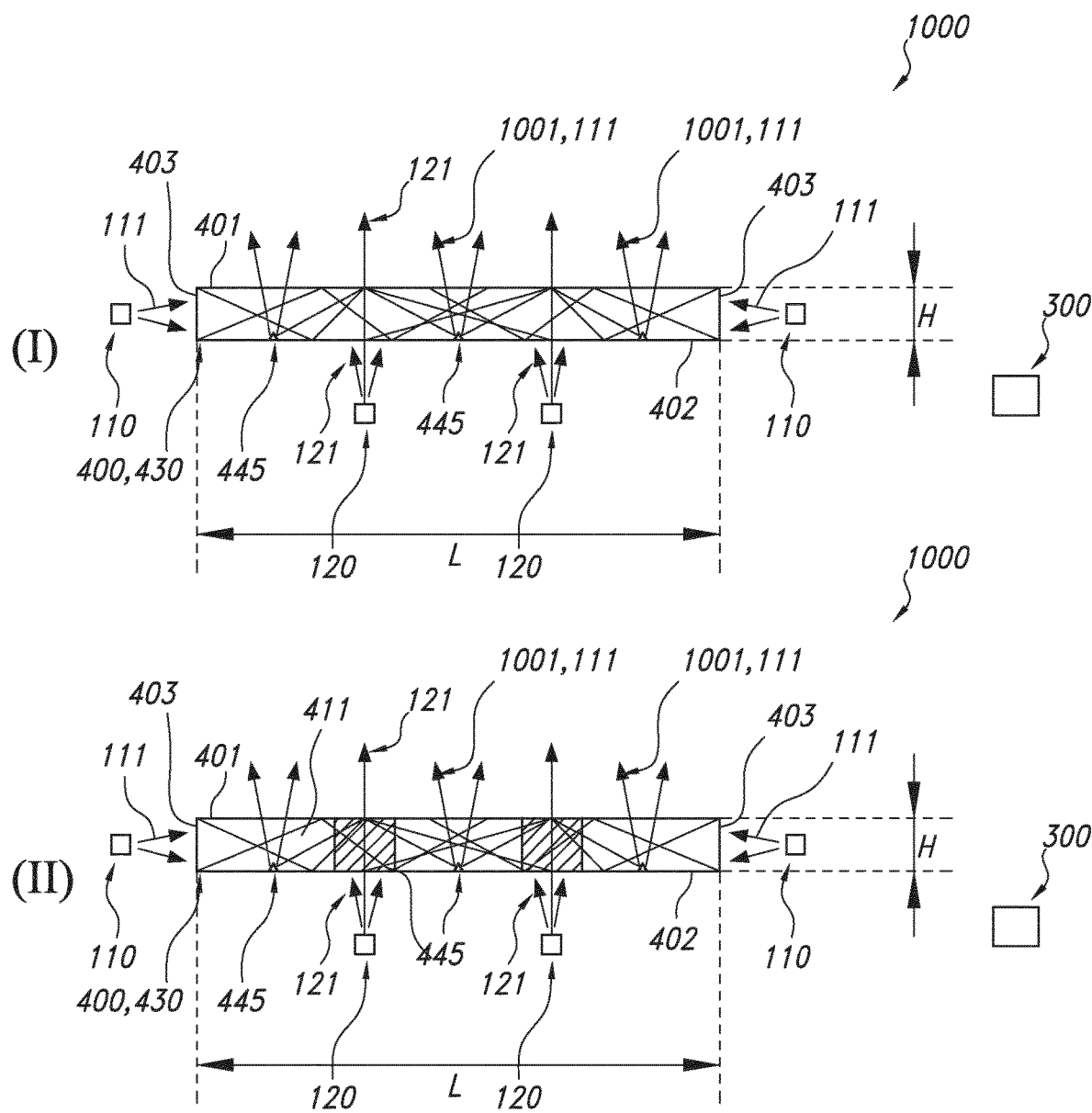
FIGS. 1a-1e schematically depict some aspects.

FIG. 1a schematically depicts some embodiments.

In a first embodiments, I, a light generating system 1000 is provided, configured to provide system light 1001. The light generating system 1000 comprises a first light generating device 110, a second light generating device 120, and a waveguide 400.

The waveguide 400 has a first face 401, a second face 402, and a side face 403 bridging the first face 401 and the second face 402

The first light generating device 110 is configured to generate first device light 111. In an operational mode, the first device light 111 may have a color point in the visible. Especially, the first light generating device 110 is configured to irradiate the side face 403. In an operational mode at least part of the first device light 111 may escape from the waveguide 400 via the first face 401. The system light 1001 may at least comprises part of the first device light that escaped from the first face 401.

The second light generating device 120 is configured to generate second device light 121. In an operational mode the second device light 121 has a centroid wavelength of at maximum 420 nm. The second light generating device 120 is configured upstream of the second face 402. In an operational mode at least part of the second device light 121 is transmitted through the waveguide 400 and escapes from the waveguide 400 via the first face 401.

Note that in this embodiment the first device light 111 and the second device light 121 may escape to the external of the system 1000 via the single (first) region. However, at least part of the first device light 111 may do so after total internal reflection whereas part of the second device light may propagate essentially perpendicular to the waveguide and escape from the waveguide without total internal reflection.

In embodiments, the one or more of the first face 401 and the second face 402 may comprise light outcouple structures 445.

The waveguide 400 may have a length L and a height H. Especially, at least part of the first device light 111 entering at one side of the waveguide will be transmitted over the entire length L and reach an opposite part, such as at least 50%. In embodiments, the absorption length is larger than L. The waveguide may have a width W (see e.g. embodiment III in FIG. 1b).

Hence, in specific embodiments, the waveguide 400 may comprise a single first region and no second regions. In such embodiments, the waveguide may essentially consist of a single first material (having a first material composition). Hence, in such embodiments the transmission of second device light through the waveguide may essentially the same over the entire waveguide; see FIG. 1a, embodiment I. As schematically depicted the single region extends from the first face to the second face of the waveguide 400.

In a second embodiment, II, a light generating system 1000 configured to provide system light 1001. The light generating system 1000 comprises a first light generating device 110, a second light generating device 120, and a waveguide 400.

The waveguide 400 has a first face 401, a second face 402, and a side face 403 bridging the first face 401 and the second face 402. Especially, the waveguide 400 comprises one or more first regions 410, comprising a first material 411 having a first material composition. Further, the waveguide 400 may comprise one or more second regions 420, comprising a second material 422 having a second material composition. Especially, the first material composition and the second material composition differ. The first region(s) and second region(s) may extend from the first face 401 to the second face 402 of the waveguide 400.

Especially, the first light generating device 110 is configured to generate first device light 111. In embodiments, in an operational mode the first device light 111 has a color point in the visible. Further, especially the first light generating device 110 may be configured to irradiate the side face 403. In an operational mode at least part of the first device light 111 may escape from the waveguide 400 via the first face 401.

The second light generating device 120 may be configured to generate second device light 121. Especially, in an operational mode the second device light 121 has a centroid wavelength of at maximum 420 nm. In embodiments, the second light generating device 120 is configured upstream of at least one of the one or more second regions 420 and configured upstream of the second face 402. Especially, the second light generating device 120 is configured to irradiate at least part of the at least one of the one or more second regions 420. In an operational mode, at least part of the second device light 121 may be transmitted through the waveguide 400 via the at least part of the at least one of the one or more second regions 420 and escapes from the waveguide 400 via the first face 401. Note that in this embodiment the second device light 121 may escape to the external of the system 1000 only via the second region(s) (and not via the first region(s)).

Reference 300 refers to a control system, which may be comprised by the light generating system 1000 or which may be functionally coupled to the light generating system 1000.

Figure 1B:
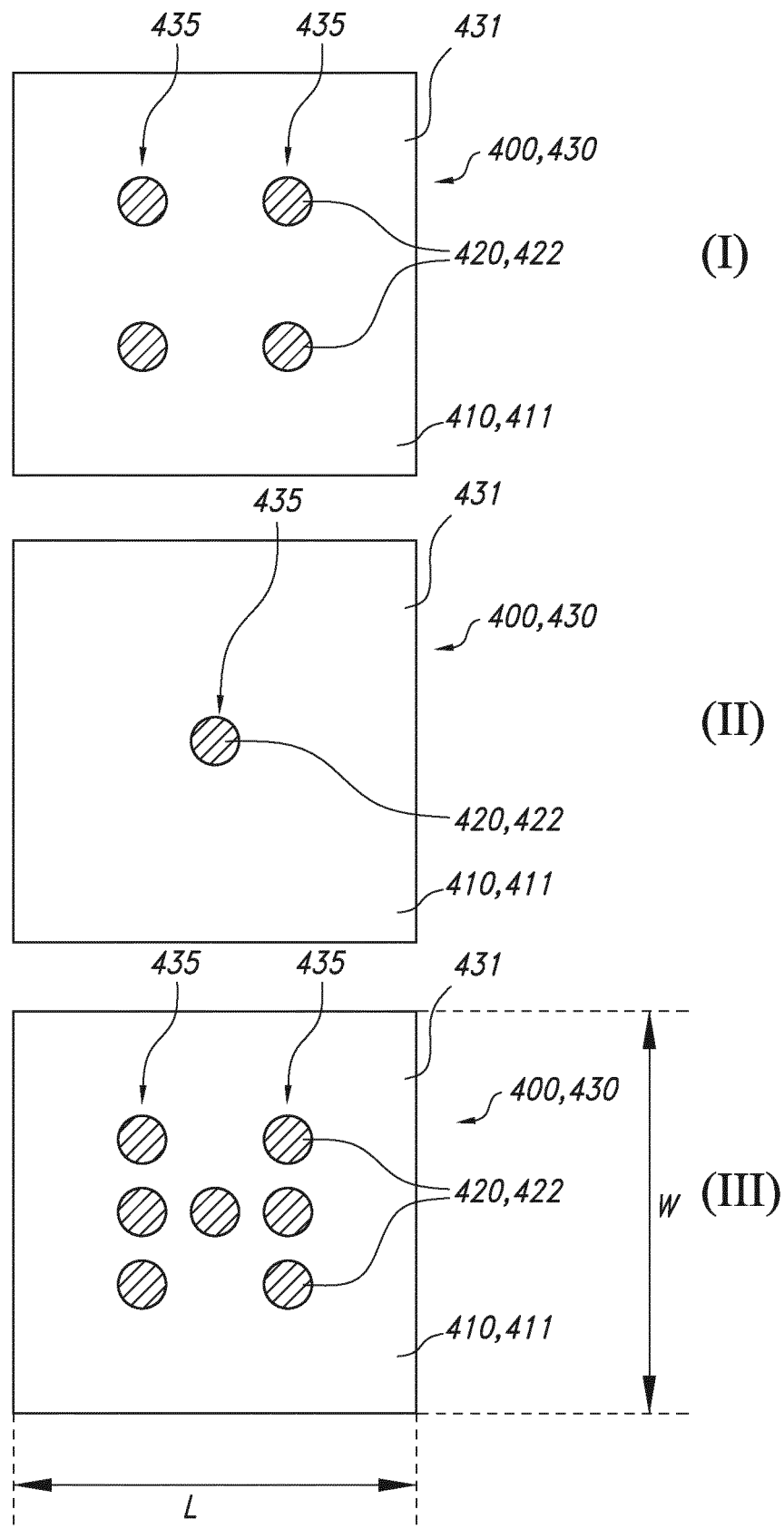

Referring to FIG. 1a, embodiment II, and embodiments I-III in FIG. 1b, a number of embodiments are described.

The one or more first regions 410 may define a first volume $V_1$ and the one or more second regions 420 may define a second volume $V_2$. Especially, in embodiments $0.01 \leq V_2/V_1 \leq 0.75$.

In embodiments, the first material 411 has a first index of refraction $n_1$ and the second material 422 has a second index of refraction $n_2$. Especially, in embodiments $0.95 \leq n_2/n_1 \leq 1.05$.

In embodiments, the second material 422 may have a higher transmission for the second light 121 than the first material 411.

In specific embodiments, the first material 411 may comprise one or more of PMMA and PC, and/or one or more of PET, PSU and PS. In specific embodiments, the second material 422 may comprise one or more of glass, quartz, ceramic, and a silicone.

In embodiments, the second light generating device 120 comprises a solid state light source. Alternatively or additionally, in embodiments the first light generating device 110 comprises a solid state light source.

In an operational mode the second device light 121 has a centroid wavelength of at maximum 380 nm. In an operational mode the first device light 111 has a centroid wavelength of at minimum 430 nm.

In an operational mode the system light 1001 may be white light. In specific embodiments, at least 90% of a spectral power of the system light 1001 in the 380-780 nm wavelength range may be defined by the first device light 111.

In specific embodiments, the light generating system 1000 may be configured to provide in a further first operational mode first device light 111 and no second device light 121. Alternatively or additionally, the light generating system 1000 may be configured to provide in in a further second operational mode, not or partly overlapping in time with the further first operational mode, second device light 121 and no first device light 111.

In embodiments, the waveguide 400 may comprise a single first region 410 and N second regions 420 enclosed by the first region 410. In embodiments, $N \geq 3$. Yet further, in embodiments $3 \leq N \leq 20$.

In specific embodiments, the light generating system 1000 may comprise a plurality of second light generating devices 420. The plurality of second light generating devices 420 and the plurality of second regions 420 may be aligned (see also FIG. 1a, embodiment II).

In embodiments, see also embodiments I-III of FIG. 1b, the waveguide 400 may comprise a waveguide plate 430. Especially, in embodiments the waveguide plate 430 may comprise a plate 431 of the first material 411 having through holes 435 filled with the second material 422.

In embodiments, each of the one or more second regions 420 may have a second region area $A_2$ in a plane of the waveguide plate 430. Further, the waveguide plate 430 may have a cross-sectional plate area $A_p$. In specific embodiments, $0.0001 \leq A_2/A_p \leq 0.1$.

As shown in e.g. embodiment I of FIG. 1b, the second regions 420 of the plurality of second regions 420 may be homogenously distributed over the waveguide 400.

Referring to embodiments II and III of FIG. 1b, the waveguide 400 may have a central part, wherein at least one of the one or more second regions 420 at least partly coincide with the central part.

Figure 1C:
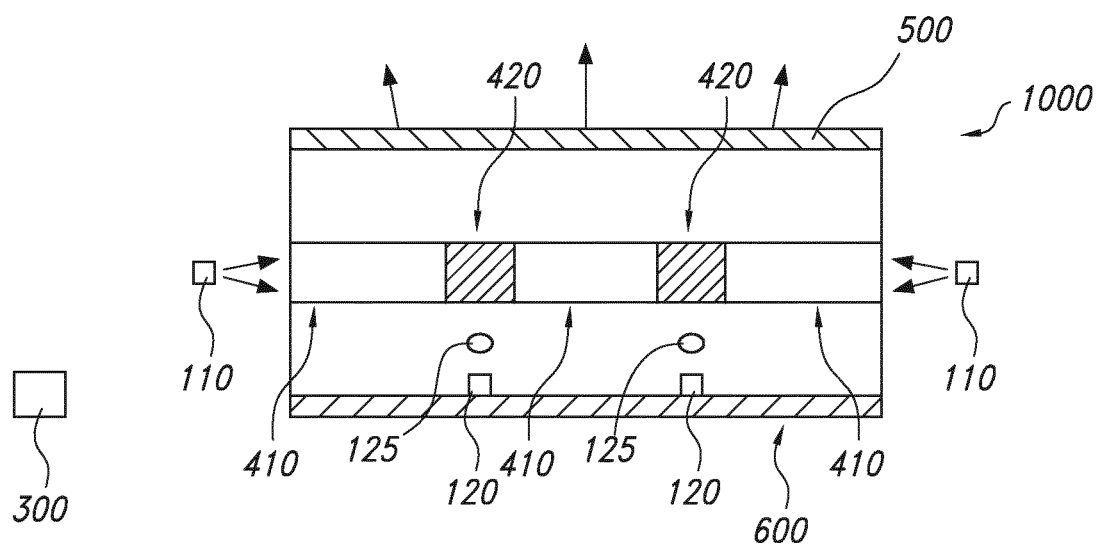

Referring to FIG. 1c, in embodiments the light generating system 1000 may further comprise a diffuser 500 configured downstream of the first face 401. The diffusor 500 may be configured to diffuse one or more of the first device light 111 and the second device light 121.

Referring to FIG. 1c, in embodiments the light generating system 1000 may further comprise a reflector 600 configured at a side of the second face 402. The reflector may be configured to reflect at least first device light 111 and in specific embodiments also second device light 121.

FIG. 1c also schematically depicts optional collimation elements 125. Such collimation element 125 may reduce the optical path length through the (second regions 420 of the) waveguide 400.

Figure 1D:
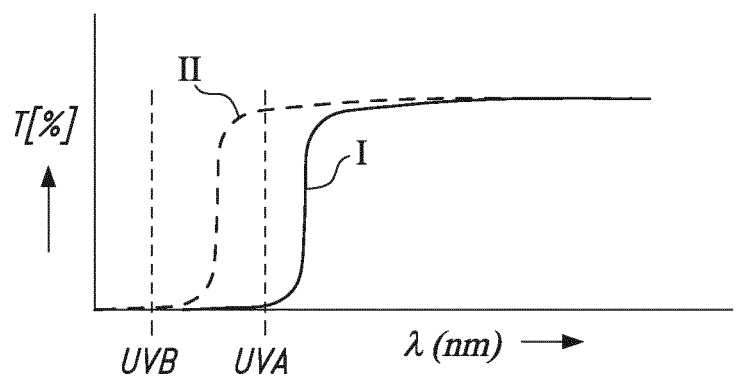

FIG. 1d schematically depict two transmission curves (transmission (%) vs. wavelength (nm)), of a first material indicated with embodiment I, and of a second material indicated with embodiment II. It is clear that the transmission for light with shorter wavelengths is better for the second material than for the first material. By way of example, a UV-A and UV-B wavelength are indicated. In this example, the second material may be used for a second light generating device having a wavelength including the UV-A wavelength(s). However, another material may have to be used would a second light generating device having a wavelength including the UV-B wavelength(s) be desirable.

Figure 1E:
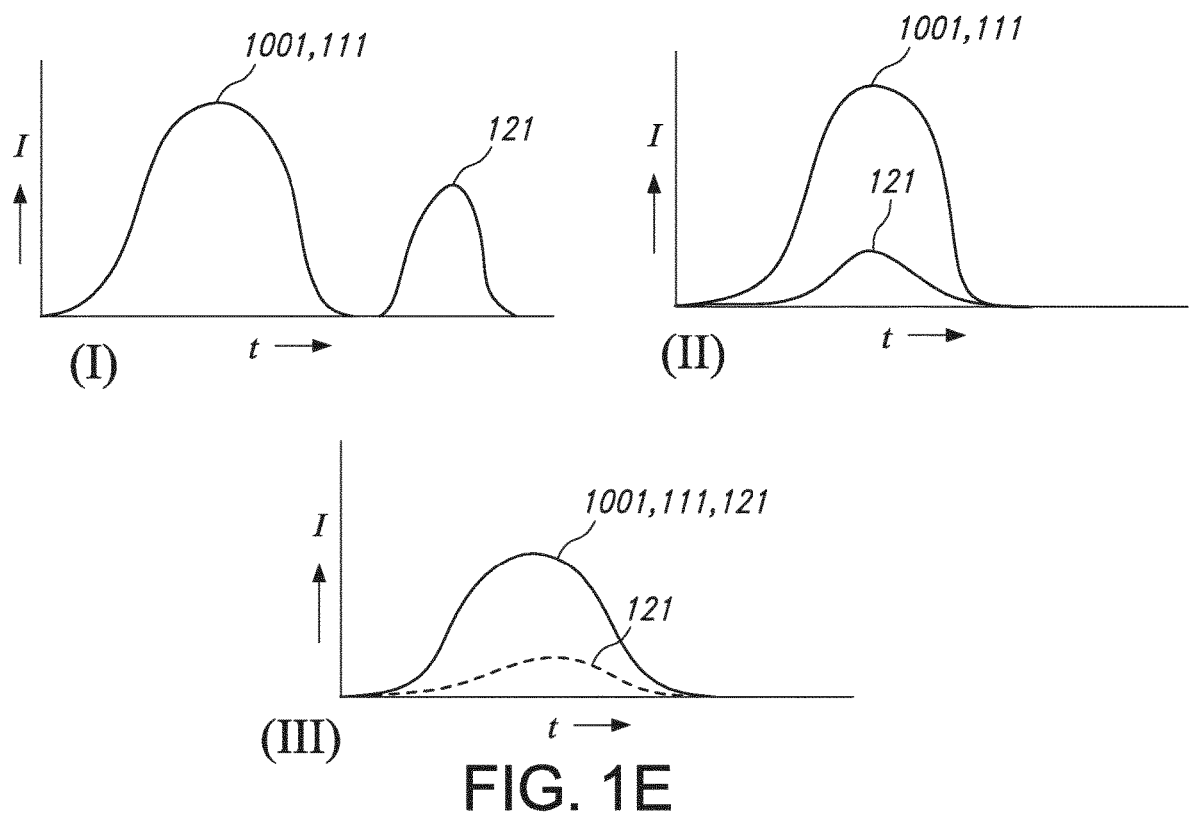

FIG. 1e schematically a number of possible embodiments. In embodiment I, the first device light 111 and the second device light 121 are provided separate in time. First system light 1001 is provided, which may consist of the first device light 111. Then functional light (radiation) may be provided, which may essentially consist of second device light 121.

In embodiment II of FIG. 1, the first device light 111 and the second device light 121, are provided at the same time. However, the second device light 121 does not contribute to the visible light, and is only functional light for e.g. air treatment or disinfection. Hence, the system light 1001 may essentially consist of the first device light 111.

In embodiment III of FIG. 1, the first device light 111 and the second device light 121, are also provided at the same time. Here, the second device light 121 does contribute to the visible light, and may have the functional of e.g. air treatment or disinfection. Hence, the system light 1001 may essentially consist of the first device light 111 and the second device light 121.

Figure 2:
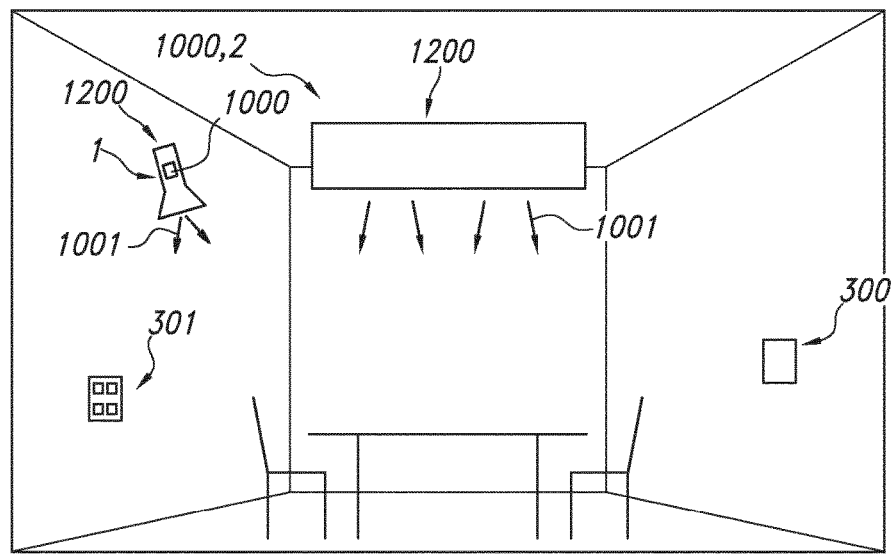
FIG. 2 schematically depict some applications.
The schematic drawings are not necessarily to scale.

FIG. 2 schematically depicts an embodiment of a luminaire 2 comprising the light generating system 1000 as described above. Reference 301 indicates a user interface which may be functionally coupled with the control system 300 comprised by or functionally coupled to the light generating system 1000. FIG. 2 also schematically depicts an embodiment of lamp 1 comprising the light generating system 1000. Hence, the invention also provides a light generating device 1200 selected from the group of a lamp 1, a luminaire 2, a disinfection device, and an optical wireless communication device, comprising the light generating system 1000 as described herein.

The term "plurality" refers to two or more.

The terms "substantially" or "essentially" herein, and similar terms, will be understood by the person skilled in the art. The terms "substantially" or "essentially" may also include embodiments with "entirely", "completely", "all", etc. Hence, in embodiments the adjective substantially or essentially may also be removed. Where applicable, the term "substantially" or the term "essentially" may also relate to 90% or higher, such as 95% or higher, especially 99% or higher, even more especially 99.5% or higher, including 100%.

The term "comprise" also includes embodiments wherein the term "comprises" means "consists of".

The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices, apparatus, or systems may herein amongst others be described during operation. As will be clear to the person skilled in the art, the invention is not limited to methods of operation, or devices, apparatus, or systems in operation.

It should be noted that the above-mentioned embodiments illustrate rather than limit the invention, and that those skilled in the art will be able to design many alternative embodiments without departing from the scope of the appended claims.

In the claims, any reference signs placed between parentheses shall not be construed as limiting the claim.

Use of the verb "to comprise" and its conjugations does not exclude the presence of elements or steps other than those stated in a claim. Unless the context clearly requires otherwise, throughout the description and the claims, the words "comprise", "comprising", and the like are to be construed in an inclusive sense as opposed to an exclusive or exhaustive sense; that is to say, in the sense of "including, but not limited to".

The article "a" or "an" preceding an element does not exclude the presence of a plurality of such elements.

The invention may be implemented by means of hardware comprising several distinct elements, and by means of a suitably programmed computer. In a device claim, or an apparatus claim, or a system claim, enumerating several means, several of these means may be embodied by one and the same item of hardware. The mere fact that certain measures are recited in mutually different dependent claims does not indicate that a combination of these measures cannot be used to advantage.

The invention also provides a control system that may control the device, apparatus, or system, or that may execute the herein described method or process. Yet further, the invention also provides a computer program product, when running on a computer which is functionally coupled to or comprised by the device, apparatus, or system, controls one or more controllable elements of such device, apparatus, or system.

The invention further applies to a device, apparatus, or system comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Further, the person skilled in the art will understand that embodiments can be combined, and that also more than two embodiments can be combined. Furthermore, some of the features can form the basis for one or more divisional applications.

Amongst others, the invention provides in embodiments a LGP (light guide panel (of waveguide panel)) based luminaire for disinfection and illumination comprising edge-lit white LEDs and back-lit UV LEDs. Edge-lit white LEDs may provide the best lighting performance (using total internal reflection), while UV light is less absorbed when the UV LEDs are used in the back-lit configuration. LG materials like PMMA or PC may be used. However, the transmission of the UV light of such materials may be less desirable. In embodiments, it is proposed to integrate at the position of the UV LED a section comprising a UV transmissive material such as silicone into the LG. The section may in embodiments not be arranged at the edge of the LG but typically in the center. Multiple sections with multiple UV LEDs may be used as well. The main light guide material may have a first refractive index n1 and the section has a second refractive index n2. In embodiments, 1.05>n1/n2>0.95 (especially useful for homogeneous lighting). In embodiments, a printed dot matrix may be printed on the section as well (for homogeneous lighting). The UV light may in embodiments collimated by a collimator upstream of the LG (to decrease the path length in the LG). The LGP is typically arranged between a reflector and an optical element such as a diffuser.

Amongst others, in embodiments the invention provides visible light emitting LEDs at the edge of a light guide, and UV-LEDs at the second (major) face of said light guide wherein the light guide is made only of a single material (the first material having the first material composition). As the UV-LEDs emit UV in the thickness direction of the light guide, the path length of the UV through the light guide may be relatively short, causing relatively small absorption.

The invention claimed is:

1. A light generating system configured to provide system light, wherein the light generating system; comprises (i) a first light generating device, (ii) a second light generating device, and (iii) a waveguide comprising a waveguide plate, wherein:
   the waveguide plate has a first face, a second face, and a side face bridging the first face and the second face;
   the first light generating device is configured to generate first device light, wherein in an operational mode the first device light has a color point in the visible; the first light generating device is configured to irradiate the side face, wherein in an operational mode at least part of the first device light escapes from the waveguide plate via the first face; and
   the second light generating device is configured to generate second device light, wherein in an operational mode the second device light has a centroid wavelength of at maximum 420 nm, and has a spectral power distribution differing from a spectral power distribution of the first device light; the second light generating device is configured upstream of the second face; wherein in the operational mode at least part of the second device light is transmitted through the waveguide plate and escapes from the waveguide plate via the first face
   wherein the waveguide plate comprises one or more first regions, comprising a first material having a first material composition, and one or more second regions, comprising a second light transmissive material having a second material composition, wherein the first material composition and the second material composition differ; and
   the second light generating device is configured upstream of at least one of the one or more second regions; wherein the second light generating device is configured to irradiate at least part of the at least one of the one or more second regions, wherein in the operational mode at least part of the second device light is transmitted through the waveguide plate via the at least part of the at least one of the one or more second regions,
   wherein the waveguide plate comprises a plate of the first material having through holes filled with the second material.

2. The light generating system according to claim 1, wherein the second light generating device comprises a solid state light source, and wherein in an operational mode the second device light has a centroid wavelength of at maximum 380 nm.

3. The light generating system according to claim 1, wherein in a basic operational mode the system light is white light, wherein at least 90% of a spectral power of the system light in the 380 nm wavelength range is defined by the first device light.

4. The light generating system according to claim 1, wherein the one or more first regions define a first volume $V_1$ and wherein the one or more second regions define a second volume $V_2$, wherein $0.01 \leq V_2/V_1 \leq 0.75$; wherein the first material has a first index of refraction n1 and wherein the second material has a second index of refraction n2, wherein $0.95 \leq n2/n1 \leq 1.05$.

5. The light generating system according to claim 1, wherein the second material has a higher transmission for the second light than the first material.

6. The light generating system according to claim 1, wherein the first material comprises one or more of PMMA and PC; and wherein the second material comprises one or more of glass, quartz, ceramic, and a silicone.

7. The light generating system according to claim 1, wherein the waveguide plate comprises a single first region and N second regions enclosed by the first region, wherein $N \geq 3$.

8. The light generating system according to claim 7, comprising a plurality of second light generating devices, wherein the plurality of second light generating devices and the plurality of second regions are aligned.

9. The light generating system according to claim 1, wherein the second regions of the plurality of second regions are homogenously distributed over the waveguide plate.

10. The light generating system according to claim 1, wherein the one or more of the first face and the second face comprise light outcouple structures.

11. The light generating system according to claim 1, wherein the light generating system is configured to provide in a further first operational mode first device light and no second device light, and in a further second operational mode, not or partly overlapping in time with the further first operational mode, second device light and no first device light.

12. The light generating system according to claim 1, further comprising a diffuser configured downstream of the first face, and configured to diffuse one or more of the first device light and the second device light, and a reflector configured at a side of the second face.

13. A light generating device selected from the group of a lamp, a luminaire, a disinfection device, and an optical wireless communication device, comprising the light generating system according to claim 1.

* * * * *